United States Patent [19]
Watson et al.

[11] B 3,998,717
[45] Dec. 21, 1976

[54] GLASS ELECTRODE FOR MEMBRANE DIFFUSION ANALYSIS OF GASES

[75] Inventors: Barry Watson, Toledo; Philip J. Breno, Oregon, both of Ohio

[73] Assignee: Owens-Illinois, Inc., Toledo, Ohio

[22] Filed: Oct. 1, 1974

[21] Appl. No.: 511,002

[44] Published under the second Trial Voluntary Protest Program on March 2, 1976 as document No. B 511,002.

[52] U.S. Cl. .......................... 204/195 P; 204/195 G
[51] Int. Cl.² .................. G01N 27/46; G01N 27/36
[58] Field of Search ............ 204/1 T, 195 P, 195 G

[56] References Cited
UNITED STATES PATENTS

| | | |
|---|---|---|
| 2,756,203 | 7/1956 | Gilbert .......................... 204/195 G |
| 3,188,285 | 6/1965 | Watanabe et al. ............ 204/195 G |
| 3,278,408 | 10/1966 | Leonard et al. ................ 204/195 P |
| 3,577,332 | 5/1971 | Porter et al. ................... 204/195 P |
| 3,649,505 | 3/1972 | Strickler et al. ............... 204/195 P |
| 3,718,567 | 2/1973 | Haddad et al. ................. 204/195 P |
| 3,830,718 | 8/1974 | Riseman et al. ................ 204/195 P |

*Primary Examiner*—T. Jung
*Attorney, Agent, or Firm*—Howard G. Bruss, Jr.; E. J. Holler

[57] ABSTRACT

This invention relates to a glass electrode structure. More specifically, the present invention relates to a glass electrode having a curved sensor tip for use in determining gas in an electrochemical membrane diffusion cell.

2 Claims, 5 Drawing Figures

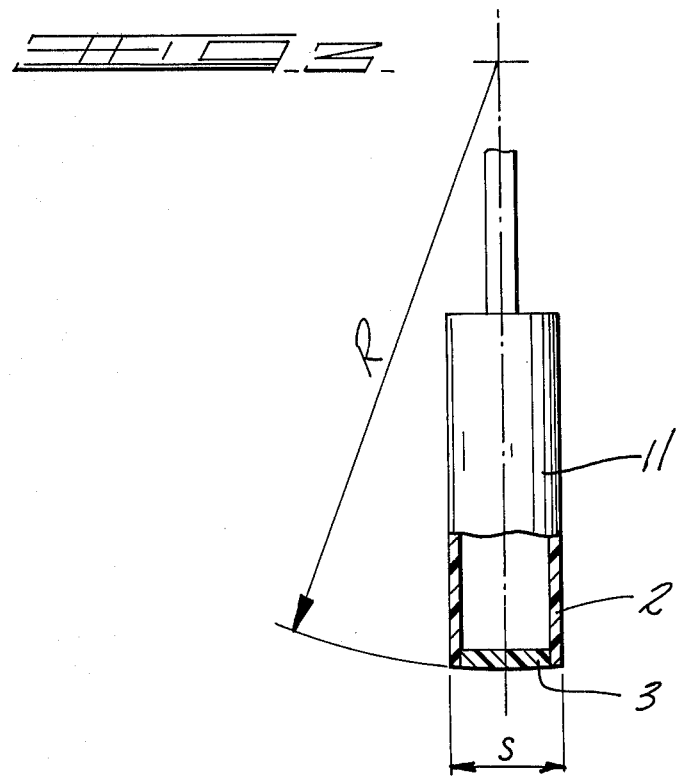
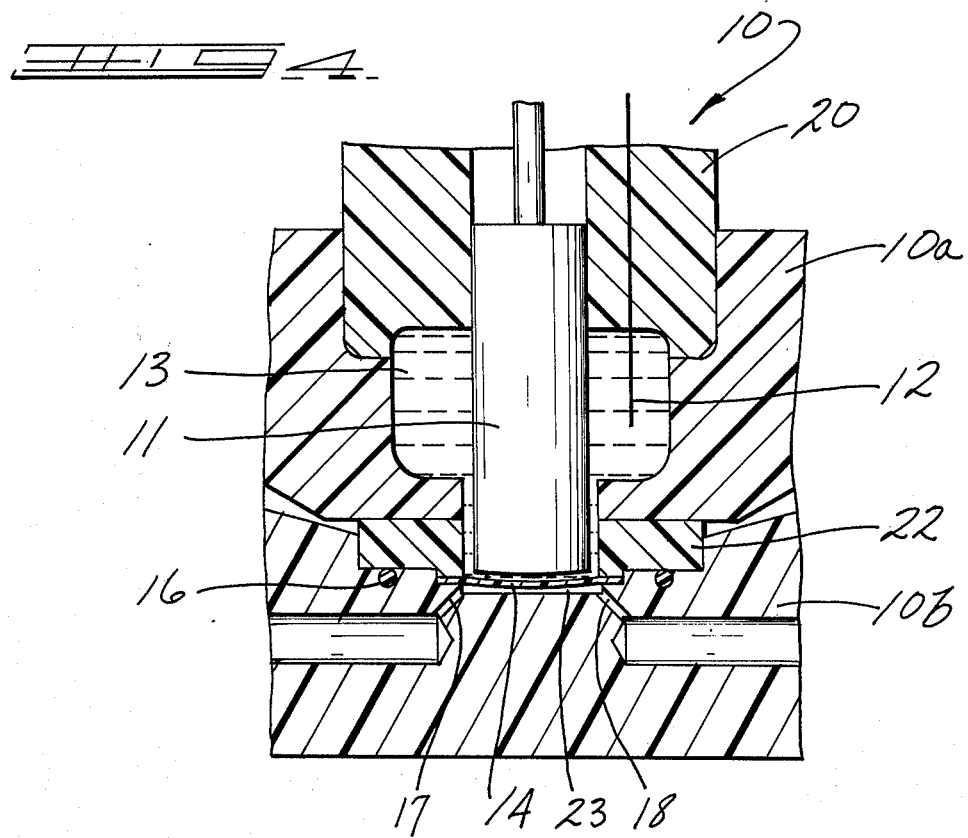

GLASS ELECTRODE FOR MEMBRANE DIFFUSION ANALYSIS OF GASES

In modern analytical techniques, the so-called "gas electrode" has found many applications. The term gas electrode as used herein is well known in the art and refers to an electrochemical cell wherein gas to be determined permeates a semipermeable membrane into an electrolyte reservoir. A pH sensitive glass sensor and reference electrode are in electrical communication with the electrolyte and the gas dissolves in the electrolyte to produce a measurable change in pH of the electrolyte. The change in pH is potentiometrically measured by the glass sensor and the response is a measure of the gas permeating the membrane.

Such gas electrodes are described in U.S. Pat. Nos. 3,649,505; 3,803,006; and commonly assigned copending application Ser. No. 427,322, filed Dec. 21, 1973 entitled "Urea Analysis", the disclosures of which are incorporated by reference.

In the particularly important application for determining urea described in application Ser. No. 427,322, the specimen is passed through a bed of immobilized urease to hydrolyze the urea to ammonium ion. The ammonium ion is then converted to ammonia by reaction with a base. The resulting ammonia gas is then selectively passed through a hydrophobic, ammonia permeable membrane for potentiometric detection with a pH sensitive electrode.

In this and other analytical techniques (such as the sulfur dioxide measurement technique of U.S. Pat. No. 3,803,006) the gas electrode can operate in either an "equilibrium" or "nonequilibrium" mode depending on the length of contact between the gas specimen and the membrane. In the equilibrium mode, the gas specimen is maintained in contact with the membrane until diffusional equilibrium is attained on both sides of the membrane. The electrolyte in contact with the membrane has a uniform pH increase throughout its volume and the potentiometric response of the electrode is precise and accurate. Unfortunately, this technique tends to be time consuming and does not lend itself to the modern analytical laboratory where many samples must be routinely processed.

In the equilibrium mode, the geometry of the sensing tip of the glass electrode and its relationship to the geometry of the membrane is not particularly critical as long as the two components are in sufficient close proximity to permit equilibration of gas concentrations on either side of the membrane.

In the nonequilibrium mode, the gas specimen is not maintained in contact with the membrane for a time sufficient to allow diffusional equilibrium to be achieved on both sides of the membrane. This produces a rapid change in the pH of the electrolyte which results in a sharp peak in the potentiometric response. Even though this potentiometric response is somewhat different from the response achieved under equilibrium conditions, the response can be calibrated for precision and accuracy as long as it is the same for like specimens.

In the nonequilibrium mode, when specimens are introduced intermittently in a flowing stream, it is important for gaseous diffusion in either direction through the membrane to occur quickly and uniformly. For instance, in application Ser. No. 427,322 the urea specimen is injected in a relatively high localized concentration in the buffered diluent stream and the reaction to produce ammonia occurs quickly. This produces a rapid increase in $NH_3$ concentration which results in a sharp peak in the potentiometric response. The sharpness of the peak is a function of the rate of change of $NH_3$ concentration (i.e. how rapidly the pH decreases depends on how rapidly the $NH_3$ back diffuses into the diluent buffered stream). The height of this sharp peak is a measure of the concentration of urea. The next urea specimen can then be injected when the potentiometric reading has returned to the base line or a point near enough to the base line such that the next urea determination is not detrimentally affected.

Under these conditions, the uniformity of the film of electrolyte between the glass sensor tip and the membrane is most important. When the layer is of uniform thickness, the gas diffusing through the membrane dissolves in an equal volume of electrolyte at all points between the glass sensor tip and the membrane. The glass sensor tip will thus "see" the same concentration of gas at all points on its surface. If the diffusion is uniform from the sample to sample, there will be no variation or drift over a prolonged series of determinations.

If the film of electrolyte between the glass sensor tip and the membrane is not uniform in the nonequilibrium mode of operation, an analytical error can be introduced, because the gas concentration in the electrolyte film varies as the function as the volume of the film and the electrode response represents an average of such concentration. Similarly, when the gas diffuses from the electrolyte through the membrane, the thinner portions of the electrolyte film will be depleted of gas more quickly than the thicker portions. As this process is repeated for several samples, substantial error can be introduced.

While such results may be suitable for many applications, a high degree of precision is required for medical analytical applications of the type of Ser. No. 427,322. The present invention provides a special pH glass sensor tip for assuring a uniform electrolyte film between such sensor tip and the membrane.

This problem has not been appreciated in prior electrode designs and the present solution to the problem is not envisioned or contemplated. For instance, the design shown in U.S. Pat. No. 3,649,505 impregnates the electrolyte into a filter paper for direct application to a bulb type electrode. No thin film of liquid electrolyte is employed.

U.S. Pat. No. 3,803,006 discloses a flat electrode tip in contact with a planar or flat membrane. When these conditions are maintained, film uniformity is assured, but such conditions are sometimes difficult to achieve. In this regard, the design of U.S. Pat. No. 3,803,006 is similar to the design shown in FIGS. 2 and 3 of application Ser. No. 427,322. When these conditions of flatness are maintained, accuracy of analysis is achieved.

In designing and constructing electrode cells for the analytical laboratory, such conditions of perfect "flatness" are not always readily achieved. Many of the membrane materials are thin films of porous plastic and are easily deformed by snug engagement with the pH sensitive glass sensor tip or the hydraulic pressure associated therewith.

The present invention provides a glass electrode sensor tip which provides for a uniform layer of electrolyte between the tip of the membrane even under conditions of snug engagement where membrane deformation has been a problem in the past.

Accordingly, the present invention provides an improved electrochemical cell for potentiometrically analyzing gaseous specimens wherein said gaseous specimen permeates a thin, flexible, semipermeable membrane of microporous plastic and dissolves in an electrolyte to cause a measurable change in pH of said electrolyte, said cell comprising a glass electrode having a pH sensitive sensor tip, a reference electrode, a reservoir of liquid electrolyte, said sensor tip and said reference electrode being in electrical communication with each other through said reservoir of electrolyte, and a membrane positioned adjacent said sensor tip to confine a thin liquid film of said electrolyte between said sensor tip and said membrane, wherein the sensor tip has a convex curvature whereby the thin film of liquid electrolyte confined between the sensor tip and the membrane is essentially of uniform thickness across the surface of said sensor tip.

Preferably for economy in manufacture and efficiency of operation, the sensor tip is formed by attaching a disc of pH sensitive glass to a chemically resistant glass tube by suitable adhesive or fusion sealing as by lampworking techniques, and then grinding and polishing the disc with a concave abrasive tool to form the desired degree of curvature to the tip.

In the preferred practice of the present invention, the chemically resistant glass tube has a diameter in the range of about 1/5 to 1/2 inch and the height of the arc of curvature of the tip of the glass sensor is in the range of about 5 to about 15 mils. When the curvature of the tip is much greater than this, for electrodes of the described geometry, the sensor is too "pointed" and film uniformity is not achieved. In the most preferred embodiment for use in the cell of Ser. No. 427,322, the tube diameter is about 1/8 inch and the height of the arc of the tip is about 5 mils to about 10 mils.

The composition of the pH sensitive glass or the chemically resistant glass tube are known in the art and form no part of the present invention. Such glass compositions and techniques for manufacture are disclosed in commonly assigned U.S. Pat. No. 3,806,440, and Chapter 9 of "Determination of pH" by Roger G. Bates (John Wiley & Sons, Inc.) 1964, the disclosures of which are incorporated by reference. Particularly of interest is glass sensor element 32 shown in the drawing of U.S. Pat. No. 3,806,440 which can be ground and polished for practicing the present invention.

The present invention will be described in conjunction with the analysis of urea with reference to the drawings wherein FIG. 1 is a schematic process flow diagram for analysis of urea;

FIG. 3 is a cross sectional illustration of a pH sensitive glass sensor tip of the present invention;

FIG. 4 is a cross sectional illustration of an electrochemical cell including the sensor tip of FIG. 3 having a uniform film of electrolyte according to the present invention.

Figure 1:
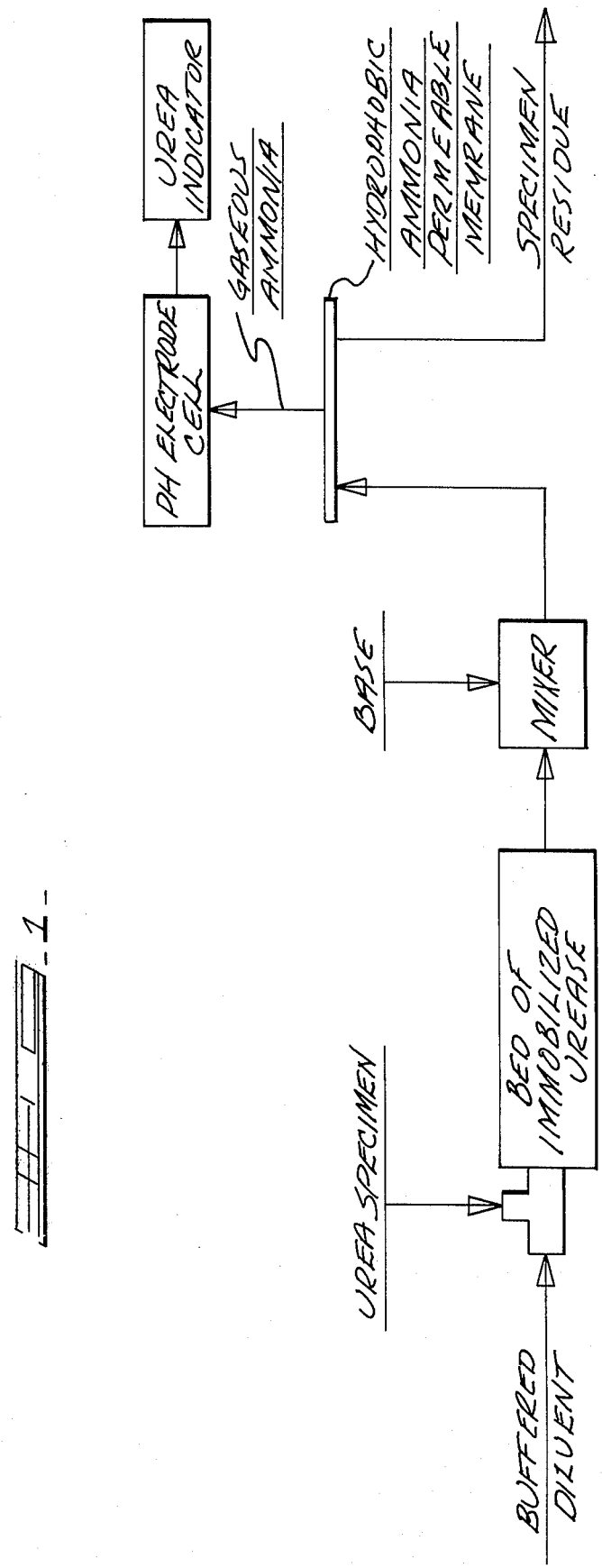

Referring now to FIG. 1, an aqueous specimen containing urea flows into a bed of immobilized urease which functions as a hydrolysis zone where the specimen is maintained for a time and at a temperature sufficient to hydrolyze urea to ammonium ions by the process of Ser. No. 427,322. Preferably the specimen is maintained in contact with the immobilized urease for a time sufficient to hydrolyze substantially all of the urea to ammonium ions. Typically, this hydrolysis is completed within a few seconds to 30 minutes or longer at temperatures ranging from 0° to about 50°C and higher. The urease is believed to be most efficient in hydrolyzing urea at a pH of about 5 to 9. Because urease is most efficient in hydrolyzing urea in the 5 to 9 pH range, the urea specimen, prior to contact with the urease, is usually mixed with an aqueous diluent which is buffered to pH 5 to 9.

The ratio of dilution of the urea specimen in the buffered diluent varies with the concentration of urea in the specimen. For physiological fluids such as blood or urine having unknown concentration within the expected concentration range, a ratio of 1 part of volume by specimen to 25 to 50 parts of diluent is suitable for an acceptable electrode response. Usually, for efficiency and economy, a small specimen (e.g. about 10 to 50 microliters) is injected into a stream of buffered diluent flowing at the rate of 0.1 to 10 ml per minute for introduction into the bed of immobilized urease. Suitable buffered diluents include 0.01M sodium citrate (pH 6.0); 0.01M sodium maleate (pH 6.2) and 0.01M tris (hydroxymethyl) aminomethane adjusted to pH 7 with HCl.

After hydrolysis of the urea, the resulting hydrolysis mixture containing ammonium ions flows from the bed of immobilized urease and is mixed with sufficient base in a suitable mixing chamber to adjust the pH of the mixture to at least about 11. At this pH and above substantially all of the ammonium ions are converted to an aqueous ammonia solution. The mixing chamber has an inlet for the hydrolyzed urea, an inlet for base, and an outlet for the resulting reaction mixture. Any type of mixer such as an impeller or blade type mixer can be used in the mixing chamber to mix the base with the hydrolyzed urea, although a small magnetically operated mixing bar has been found to be quite satisfactory.

Any type of base which does not contain ammonia or ammonium ion can be used to adjust the pH to at least about 11. Suitable bases include the alkaline earth metal hydroxides [e.g. $Ca(OH)_2$ or $Mg(OH)_2$] although dilute aqueous solutions of alkali metal hydroxides, particularly NaOH, having concentrations in the range of about 0.01 to about 1N are preferred for efficiency and economy in pH adjustment.

After adjustment of the pH to at least 11, the resulting aqueous ammonia solution is contacted with a hydrophobic, ammonia permeable membrane for a time sufficient to allow gaseous ammonia to permeate through the membrane. Such hydrophobic membranes permit the passage of gaseous ammonia while retaining aqueous solutions and can be in the form of hydrophobic porous and microporous plastic films having a thickness of about 0.1 to about 10 mils, a porosity of about 10 to 85% and a pore size diameter of about 0.05 to 5 microns. Suitable plastic membranes are commercially available in the form of porous copolymers of acrylonitrile and vinyl chloride on nylon support (Acropor™ sold by Gelman Instrument Company) porous hydrophobic cellulose acetate, porous polytetrafluoroethylene (Teflon™ sold by DuPont), microporous polypropylene (Celgard™ sold by Celanese Corporation), porous polyvinylidene fluoride and other membrane materials as disclosed in U.S. Pat. No. 3,649,505 the disclosure of which is incorporated by reference. These membranes permit diffusion of gaseous ammonia while monovalent ions such as $Na^+$, $K^+$, or $Li^+$, remain in the aqueous solution which does not diffuse through the membrane.

The gaseous ammonia permeating the membrane is then passed to an electrochemical cell which contains an aqueous electrolyte solution. The gaseous ammonia dissolves in this electrolyte solution to increase the pH of the electrolyte solution. This increase in pH is potentiometrically measured with a pH sensitive electrode.

The electrolyte solution is usually a dilute solution of an ammonium salt (e.g. $-0.1M$ $NH_4Cl$) to provide base line ammonium ion concentration from which an increase in pH is readily measurable. This increase in pH is a function of the amount of ammonia gas permeating through the membrane and the corresponding potentiometric reading on the electrometer can be readily converted to the urea equivalent of the original specimen. The urea equivalent of the original specimen is usually reported in mg blood urea nitrogen (i.e. BUN)/100 ml specimen. These units are conventional in clinical applications.

Figure 2:
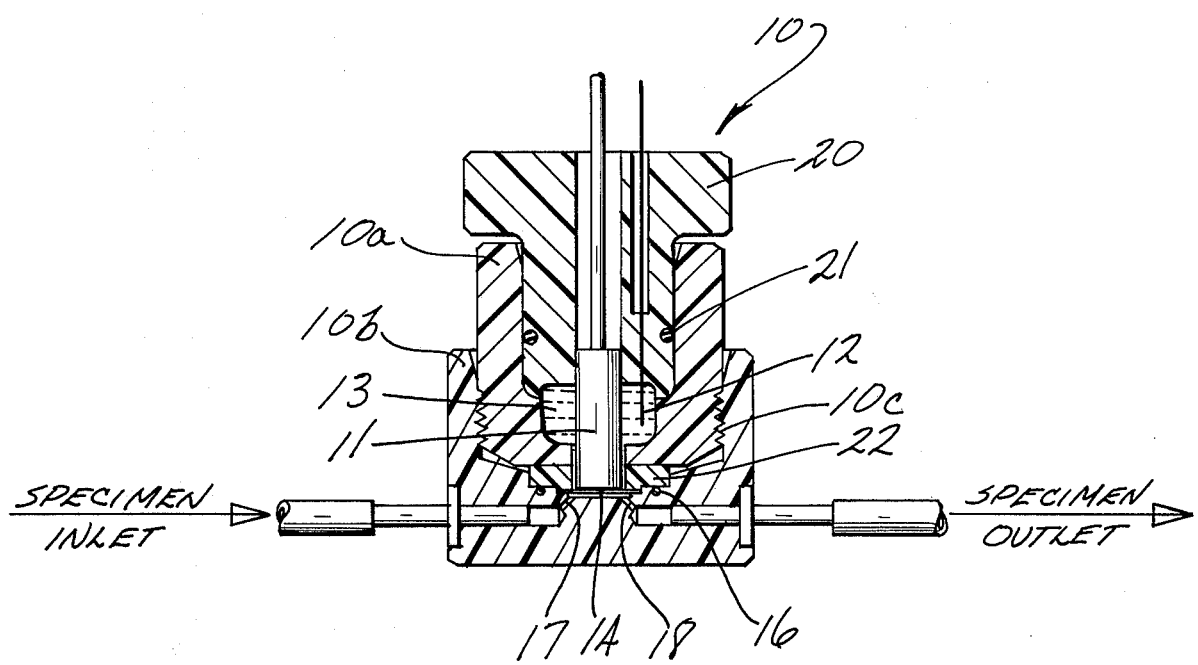
FIG. 2 is a cross sectional illustration of an electrochemical cell of the prior art and FIG. 2A is a blown up view of the cell of FIG. 2 where the film of electrolyte between the sensor tip and the membrane is not uniform.
Figure 2A:
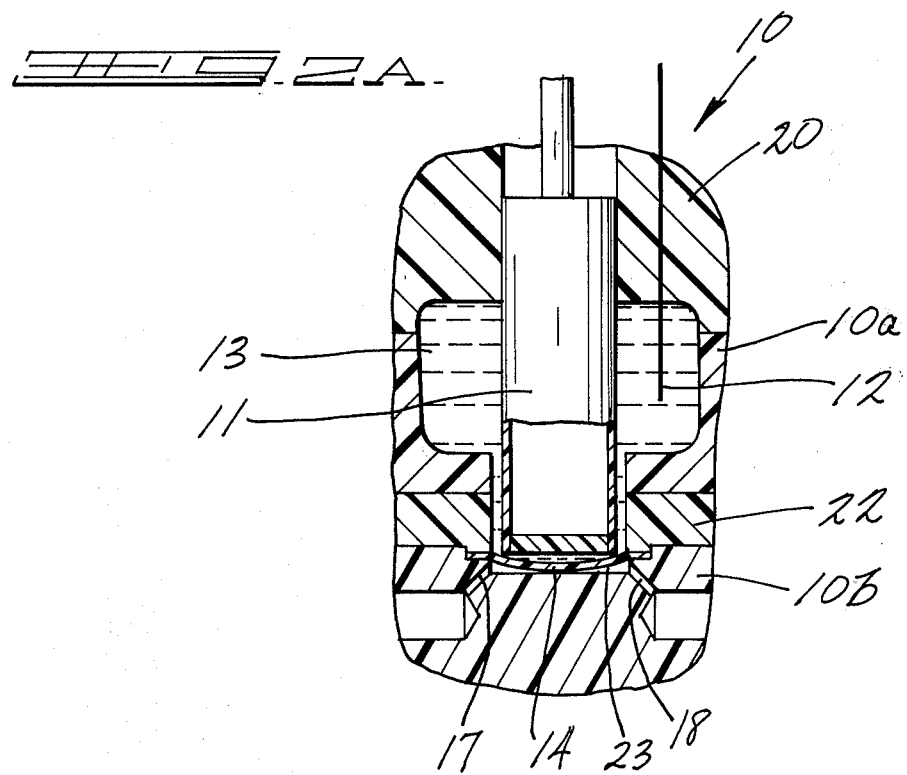

FIG. 2 and FIG. 2A are cross sectional illustrations of an electrochemical cell wherein a flat bottom sensor tip of the prior art is used.

FIG. 3 is a cross sectional illustration of a glass electrode component generally indicated by reference numeral 11 comprising a chemically resistant glass tube 2 to which is fusion sealed a convex pH glass sensor tip 3 having a pH sensitive glass composition. The curvature of the tip 3 is described in terms of the radius of curvature of the circle which generally describes such curvatures. This radius of curvature is designated R in FIG. 3. When R is about 2.5 inches, the height of arc (i.e. the maximum distance between the chord subtended by arc S, and arc S) is about 5 mils, and when R is about 1 inch the height of the arc is about 15 mils for glass tube 2 having an outside diameter of about ⅛ inch.

For practical efficiency, the height of the arc of the glass tip 3 is in the range of about 5 to about 15 mils and usually in the range of about 5 to about 10 mils.

The convex curvature is produced by grinding and polishing with a fine concave abrasive tool having a radius of curvature of 2.5 inches. The outside diameter of tube 2 is in the range of about 1/5 inch to about ½ inch with about ⅛ inch being typical.

FIG. 4 is a broken away enlargement of a cell like FIG. 2 using a convex sensor tip of FIG. 3. In FIGS. 2 and 4 electrochemical cell 10 comprises an electrode chamber 10a to which membrane housing 10b is engaged by means of screw threads 10c. Chamber 10a contains a pH sensitive glass electrode 11 which can be a conventional glass electrode composition referenced against a suitable conventional reference standard electrode 12 such as a platinum wire coated with silver/silver chloride. Both of those electrodes are held in position by electrode support 20 equipped with gasket 21. Electrodes 11 and 12 are electrically connected to a conventional potentiometric pH meter which is not shown.

The sensor tip of electrodes 11 in FIG. 2 and FIG. 4 extend into electrolyte cavity 13 which contains an aqueous 0.1M $NH_4Cl$ solution. Reference electrode 12 also extends into electrolyte cavity 13. The bottom of electrolyte cavity 13 is defined by hydrophobic, ammonia permeable membrane 14 and the sensing tips are positioned adjacent thereto. Membrane 14 is held in contact with electrolyte cavity 13 by membrane housing 10b and membrane holder 22. A liquid seal is maintained by means of gasket 16. Membrane housing 10b is also provided with a narrow passageway 17 through which the sample containing the ammonia flows in permeation chamber 23. The passageway 17 and permeation chamber 23 are of such dimensions to assure turbulent flow therein for maximum exposure of the sample to membrane 14 to allow efficient ammonia permeation. After contact with membrane 14 the specimen residue which is depleted in ammonia leaves through passageway 18. The potentiometric measurement which results from the increase in pH is converted to the urea concentration of the original urea specimen by conventional potentiometric calibration techniques.

In FIG. 2A sensor tip of electrode 11 is flat and the membrane 14 is shown as being slightly "bowed" as happens when the sensor tip is not inserted carefully and properly. In FIG. 4 the sensor tip has an arc height of 7 mils and is positioned so that membrane 14 is depressed about 10 mils from the planar, horizontal position. A uniform thickness of electrolyte is confined therebetween.

The invention will be further illustrated in the examples that follow wherein all parts are parts by weight, all percentages are weight percentages, and all temperatures are in °C unless stated otherwise.

EXAMPLE 1

In Example 1 the buffered diluent is an aqueous 0.01M solution of tris (hydroxymethyl) aminomethane which has been adjusted to pH 7.5 (with HCl) and is 0.17M in NaCl, $1.0 \times 10^{-3}M$ in disodium ethylene diamine tetraacetic acid, and $1.0 \times 10^{-5}M$ in $NH_4Cl$.

The base used to adjust the pH is a 0.03N sodium hydroxide solution.

The immobilized urease is prepared by immobilizing urease on porous alumina powder as described in Example 5 of Ser. No. 427,322.

The electrochemical cell uses a glass electrode having a pH sensitive sensor tip as shown in FIG. 4 with an arc height of about 7 mils. The electrode has a silver-silver chloride element in HCl electrolyte referenced against a silver-silver chloride electrode. This is conventional and is not shown.

The ammonia permeable hydrophobic membrane is a microporous polypropylene film having a thickness of 1 mil, porosity of 35%, an average pore diameter of less than 0.1 microns obtained from Celanese Corporation under the trade name of "Celgard 2400."

The electrolyte in cavity 13 is 0.1M $NH_4Cl$.

The buffered diluent and base solutions described above are pumped through the apparatus described in FIG. 1 at a rate of 1.0 ml/min. for each stream. Several 10 microliter samples of each of the aqueous urea specimen concentration described below are quickly injected with a hypodermic needle through the injection "tee" into the immobilized enzyme column as shown in FIG. 1. The analysis takes place as described above in conjunction with the drawing. Calibration is done with aqueous urea samples of known composition as in Ser. No. 427,322.

Standard blood serum specimens are then analyzed in a single series of determinations with one sample injected immediately after analysis of the previous sample. The "Test Number" indicates the order of analysis. The standard serum specimens are supplied as having the following BUN content.

| Serum Specimen | mg BUN/100 ml |
|---|---|
| A | 12.2 |
| B | 16.0 |
| C | 30.7 |
| D | 48.0 |

Upon analysis by the present invention as described above, the following results are obtained. The millivolt response is negative.

| | Specimen A | | | Specimen B | | | Specimen C | | | Specimen D | |
|---|---|---|---|---|---|---|---|---|---|---|---|
| Test No. | Millivolt Response | BUN mg/100 ml | Test No. | Millivolt Response | BUN mg/100 ml | Test No. | Millivolt Response | BUN mg/100 ml | Test No. | Millivolt Response | BUN mg/100 ml |
| 1 | 100.5 | 12.3 | 7 | 109 | 17.4 | 4 | 125.0 | 32.4 | 10 | 136.5 | 50.4 |
| 2 | 101.0 | 12.6 | 8 | 109 | 17.4 | 5 | 125.5 | 33.0 | 11 | 136.5 | 50.4 |
| 3 | 101.5 | 12.7 | 9 | 109 | 17.4 | 6 | 126.0 | 33.3 | 12 | 136.5 | 50.4 |
| 13 | 103.5 | 13.7 | 19 | 109 | 17.4 | 16 | 125.5 | 33.0 | 22 | 136.5 | 50.4 |
| 14 | 102.0 | 13.2 | 20 | 109 | 17.4 | 17 | 125.5 | 33.0 | 23 | 136.5 | 50.4 |
| 15 | 102.0 | 13.2 | 21 | 109 | 17.4 | 18 | 125.5 | 33.0 | 24 | 136.5 | 50.4 |
| Average Reading | 101.75±0.95 | | | 109.0±0.0 | | | 125.5±0.2 | | | 136.5±0.0 | |
| BUN mg/100 ml | 13.0±1.0 | | | 17.4±0.0 | | | 33.0±0.4 | | | 50.4±0.0 | |

EXAMPLE 2

The procedures of Example 1 are repeated except that a fresh microporous polypropylene membrane is used. The results are reported below.

| | Specimen A | | | Specimen B | | | Specimen C | | | Specimen D | |
|---|---|---|---|---|---|---|---|---|---|---|---|
| Test No. | Millivolt Response | BUN mg/100 ml | Test No. | Millivolt Response | BUN mg/100 ml | Test No. | Millivolt Response | BUN mg/100 ml | Test No. | Millivolt Response | BUN mg/100 ml |
| 1 | 93.0 | 12.2 | 7 | 100.5 | 16.5 | 10 | 116.5 | 31.6 | 4 | 126.5 | 46.5 |
| 2 | 93.0 | 12.2 | 8 | 100.0 | 16.2 | 11 | 117.0 | 32.4 | 5 | 127.5 | 49.0 |
| 3 | 93.0 | 12.2 | 9 | 100.0 | 16.2 | 12 | 117.5 | 32.9 | 6 | 127.5 | 49.0 |
| 13 | 94.0 | 12.6 | 19 | 100.5 | 16.5 | 22 | 117.5 | 32.9 | 16 | 127.5 | 49.0 |
| 14 | 94.0 | 12.6 | 20 | 100.5 | 16.5 | 23 | 118.0 | 33.3 | 17 | 128.0 | 49.8 |
| 15 | 94.0 | 12.6 | 21 | 100.5 | 16.5 | 24 | 117.5 | 32.9 | 18 | 128.0 | 49.8 |
| Average Reading | 93.5 | | | 100.3 | | | 117.3 | | | 127.5 | |
| BUN mg/100 ml | 12.4±0.2 | | | 16.4±0.2 | | | 32.4±0.4 | | | 48.9±0.3 | |

The above data for Examples 1 and 2 indicates that the results remain "precise" over a prolonged series of determinations even when specimens of various concentrations of BUN are intermittently analyzed.

CONTROL

For the purpose of comparison, an electrochemical cell like that shown in FIG. 2 is used. The sensor tip of electrode 11 is flat and is depressed against a microporous polypropylene membrane as described above with a nonuniform layer of electrolyte therebetween. The membrane is deflected approximately 10 mils from its initial planar horizontal position. The procedures are essentially the same as in Example 1.

Seven 20 microliter samples each of two standard blood serum specimens are analyzed after calibration with aqueous urea standards in a similar manner as for Example 1 and the results are set forth below. The "Test Number" corresponds to the order of specimen injection.

| | Normal Serum Urea | | | Abnormal Serum Urea | |
|---|---|---|---|---|---|
| Test No. | Millivolt Response | BUN mg/100 ml | Test No. | Millivolt Response | BUN mg/100 ml |
| 1 | 67.0 | 17.4 | 2 | 41.5 | 53.8 |
| 3 | 66.0 | 18.1 | 4 | 40.5 | 56.0 |
| 5 | 66.0 | 18.1 | 6 | 40.0 | 57.4 |
| 7 | 66.0 | 18.1 | 8 | 39.5 | 58.8 |
| 9 | 65.0 | 18.9 | 10 | 39.0 | 60.2 |
| 11 | 65.0 | 18.9 | 12 | 39.5 | 58.8 |
| 13 | 65.0 | 18.9 | 14 | 38.5 | 61.6 |

The millivolt response is positive for these determinations. The drift or lack of "precision" in the millivolt response, indicates higher concentrations of urea, later in the series of tests.

Having thus described the invention, What is claimed is:

1. In an electrochemical cell for potentiometrically analyzing gaseous specimens wherein said gaseous specimen permeates a thin, flexible, semipermeable membrane of microporous polyproplyene and dissolves in an electrolyte to cause a measurable change in pH of said electrolyte, said cell comprising a glass electrode having a pH sensitive sensor tip, a reference electrode, a reservoir of liquid electrolyte, said sensor tip and said reference electrode being in electrical communication with each other through said reservoir of electrolyte, and said membrane being spaced from but positioned adjacent said sensor tip to confine a thin liquid film of said electrolyte without a spacer between said sensor tip and said membrane; the improvement wherein the outer surface of said sensor tip has a convex curvature defined by a radius of curvature of between about 1 inch and about 2.5 inches, said sensor tip being attached to a chemically resistant glass tube having a diameter of about ⅛ inch at the point of attachment to define the height of the arc of said tip in the range of about 5 to about 15 mils whereby the thin film of liquid electrolyte confined between the sensor tip and the membrane is essentially of uniform thickness across the surface of said sensor tip.

2. The electrochemical cell of claim 1 wherein the height of the arc of said tip is about 5 to about 10 mils.

* * * * *